(12) United States Patent
Myers et al.

(10) Patent No.: US 11,283,975 B2
(45) Date of Patent: Mar. 22, 2022

(54) EYE IMAGE CAPTURING

(71) Applicant: Welch Allyn, Inc., Skaneateles Falls, NY (US)

(72) Inventors: Thomas A. Myers, Syracuse, NY (US); Christian H. Reinke, York, SC (US); Carlos A. Suarez, Syracuse, NY (US); Ynjiun P. Wang, Cupertino, CA (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 172 days.

(21) Appl. No.: 16/230,315

(22) Filed: Dec. 21, 2018

(65) Prior Publication Data
US 2020/0204710 A1   Jun. 25, 2020

(51) Int. Cl.
| | | |
|---|---|---|
| *A61B 3/14* | (2006.01) |
| *H04N 5/225* | (2006.01) |
| *G02B 7/04* | (2021.01) |
| *G06K 9/00* | (2022.01) |
| *A61B 3/12* | (2006.01) |

(52) U.S. Cl.
CPC ............ *H04N 5/2254* (2013.01); *A61B 3/12* (2013.01); *A61B 3/14* (2013.01); *G02B 7/04* (2013.01); *G06K 9/0061* (2013.01); *G06K 9/00604* (2013.01); *H04N 5/2253* (2013.01); *H04N 5/2256* (2013.01)

(58) Field of Classification Search
CPC ........... A61B 3/12; A61B 3/14; A61B 3/0033; A61B 3/0058
USPC ....................................................... 351/206
See application file for complete search history.

(56) References Cited

U.S. PATENT DOCUMENTS

| | | | |
|---|---|---|---|
| 6,547,394 B2 | 4/2003 | Doherty | |
| 2009/0096988 A1 | 4/2009 | Fink | |
| 2009/0153797 A1* | 6/2009 | Allon | A61B 3/12 351/206 |
| 2012/0220850 A1 | 8/2012 | Umekawa | |
| 2014/0267668 A1* | 9/2014 | Ignatovich | A61B 3/125 348/78 |
| 2015/0230701 A1 | 8/2015 | Sato et al. | |

(Continued)

FOREIGN PATENT DOCUMENTS

| | | |
|---|---|---|
| JP | 10137189 H | 5/1998 |
| JP | 2015027357 A | 2/2015 |

(Continued)

OTHER PUBLICATIONS

Extended European Search Report for Application No. 19218334.1 dated May 11, 2020.

(Continued)

*Primary Examiner* — Mahidere S Sahle
(74) *Attorney, Agent, or Firm* — Merchant & Gould P.C.

(57) ABSTRACT

An imaging device includes a housing having a surface that can engage the face of a patient. A cavity is at least partially defined by the surface. An anterior imaging system includes an optical lens barrel positioned inside the cavity, and the optical lens barrel includes a variable focus lens at one end and an image sensor array at an opposite end. One or more illumination LEDs are positioned around the periphery of the optical lens barrel at opposite sides of the variable focus lens, and are configured to illuminate the cavity to capture images of an anterior of the eye.

8 Claims, 11 Drawing Sheets

(56) References Cited

U.S. PATENT DOCUMENTS

| | | |
|---|---|---|
| 2015/0245765 A1 | 9/2015 | Fujii et al. |
| 2017/0119241 A1 | 5/2017 | Farchione et al. |
| 2017/0119250 A1* | 5/2017 | Kolachalama ............ A61B 3/10 |
| 2018/0220888 A1 | 8/2018 | Tumlinson et al. |
| 2018/0344156 A1 | 12/2018 | Farberov |
| 2019/0365224 A1 | 12/2019 | Kook et al. |

FOREIGN PATENT DOCUMENTS

| | | |
|---|---|---|
| JP | 2017080151 A | 5/2017 |
| JP | 2018038496 A | 3/2018 |
| WO | 2018013923 A1 | 1/2018 |
| WO | 2018/143651 A1 | 8/2018 |

OTHER PUBLICATIONS

U.S. Appl. No. 16/229,939, filed Dec. 21, 2018.
Examination Report for Australian Application No. 2019283800 dated May 22, 2020, 9 pages.

* cited by examiner ical professionals use cameras during eye
EYE IMAGE CAPTURING Trained medical professionals use cameras during eye examinations for diabetic retinopathy screening. The cameras can produce images of the back of the eye such as the retina and optic disc, and those images can be used to diagnose and treat diabetic retinopathy.

In addition to taking images of the retina and optic disc, it may be desirable to take exterior images of the front of the eye to screen for anterior damage and deformities. For example, a corneal abrasion is a scratch on the cornea of the eye, and can result from flying dust, specks of metal, grains of sand, or other foreign objects that can scratch the exterior surface of the eye.

SUMMARY

In one aspect, an anterior imaging system comprises an optical lens barrel including a camera and a lens; and one or more illumination LEDs positioned around the periphery of the optical lens barrel, and configured to illuminate an eye so that images of the eye can be captured. In some examples, the LEDs are positioned around the periphery of the optical lens barrel within a cavity inside a housing of an imaging device.

In another aspect, an imaging device comprises a housing having a surface configured to engage the face of a patient; a cavity at least partially defined by the surface; an anterior imaging system having an optical lens barrel positioned inside the cavity and having a variable focus lens at one end, and an image sensor array at an opposite end; one or more illumination LEDs positioned around the periphery of the optical lens barrel at opposite sides of the variable focus lens, and configured to illuminate the cavity; and a processing device and at least one non-transitory computer readable data storage device storing instructions that, when executed by the processing device, cause the imaging device to coordinate the illumination of the one or more illumination LEDs with adjustments of the variable focus lens to capture an image of the eye.

In another aspect, a method for capturing eye images comprises: receiving initiation of a workflow to capture one or more eye images; moving an optical lens barrel along x, y, and z axes to position the optical lens barrel proximate a first eye; coordinating the illumination of one or more illumination LEDs with adjustments of a variable focus lens to capture an image of the first eye; moving the optical lens barrel along the along x, y, and z axes to position the optical lens barrel proximate a second eye; coordinating the illumination of the one or more illumination LEDs with adjustments of the variable focus lens to capture an image of the second eye; and storing the one or more images of the first eye and the second eye.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
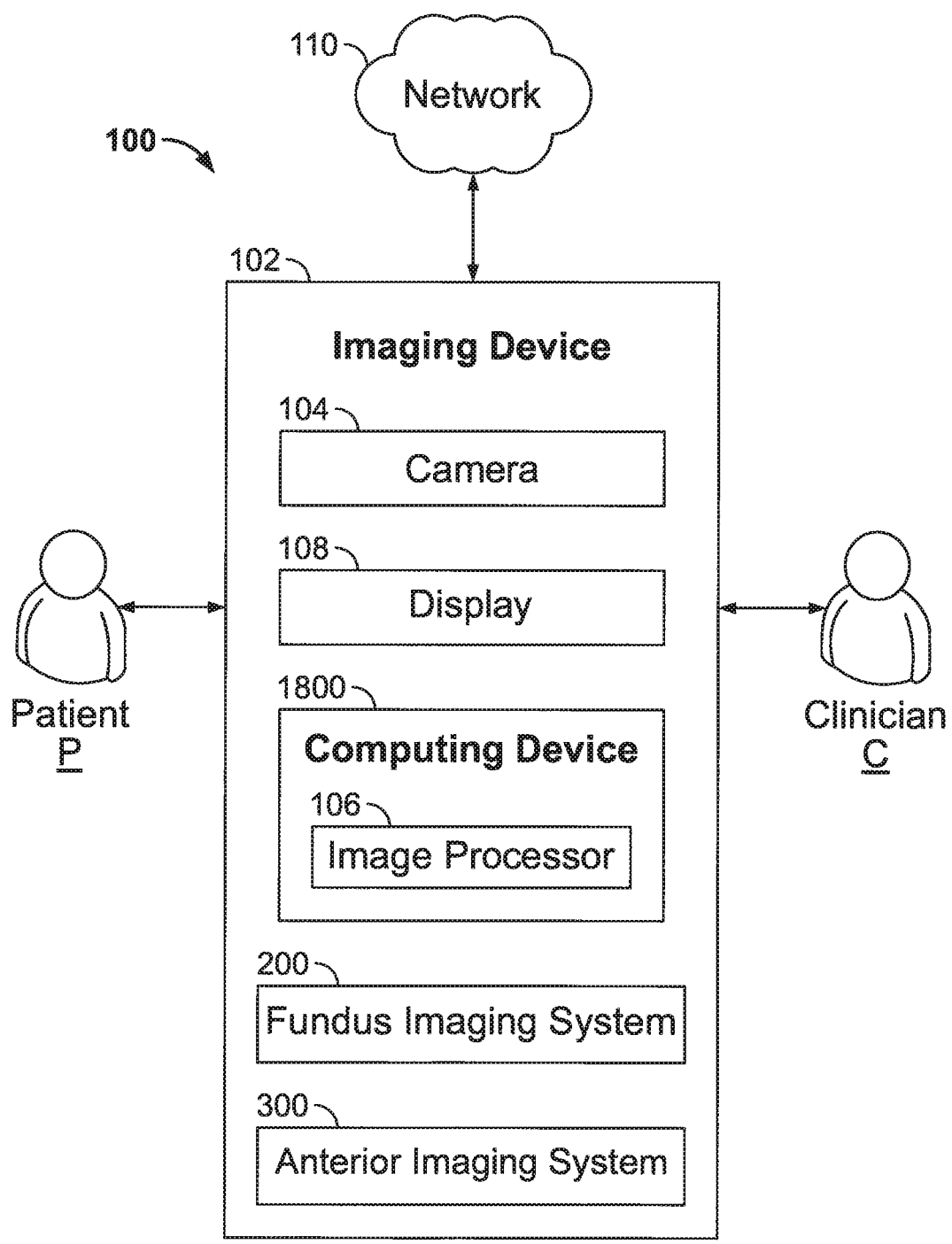
FIG. 1 is a schematic block diagram of an example system for capturing images of the eye of a patient under examination by a clinician.

FIG. 1 is a schematic block diagram illustrating an example system 100 for capturing and viewing images of the eye of a patient P under examination by a clinician C. The system 100 includes the patient P, the clinician C, an imaging device 102, and a network 110.

The imaging device 102 includes a computing device 1800 (see FIG. 17) having an image processor 106. The imaging device 102 further includes a camera 104, a display 108, a fundus imaging system 200, and an anterior imaging system 300. Each of the foregoing components of the imaging device 102 are in communication with the computing device 1800.

Figure 2:
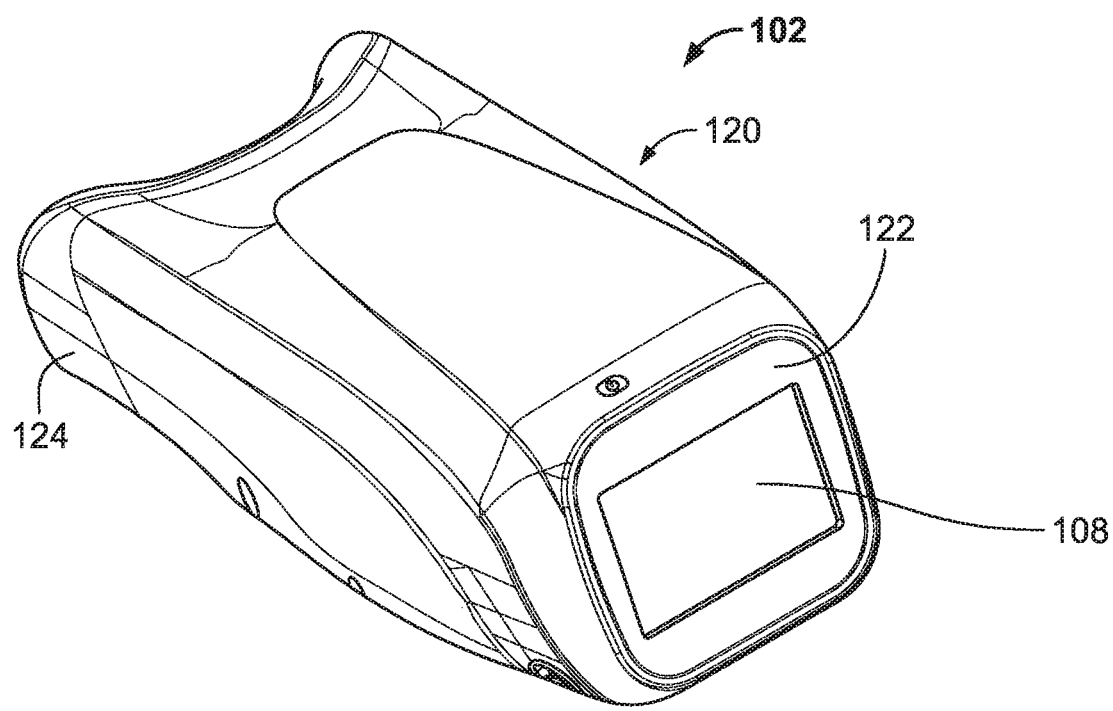
FIG. 2 is an isometric view of an example imaging device.
Figure 3:
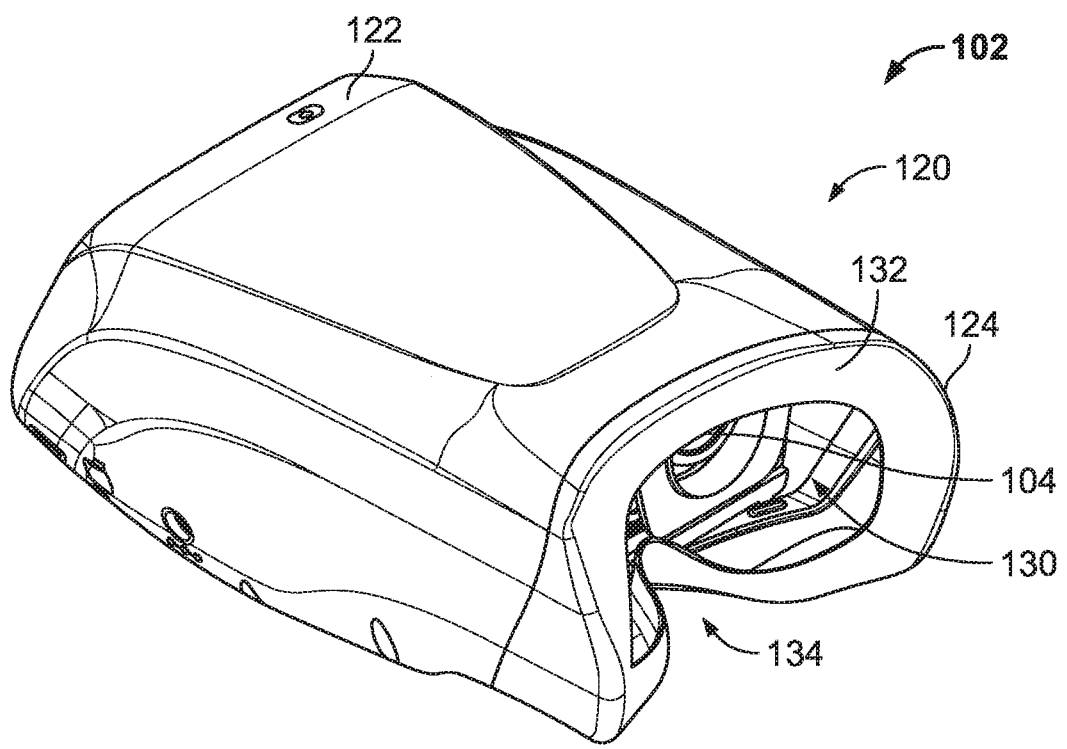
FIG. 3 is another isometric of the example imaging device.
Figure 4:
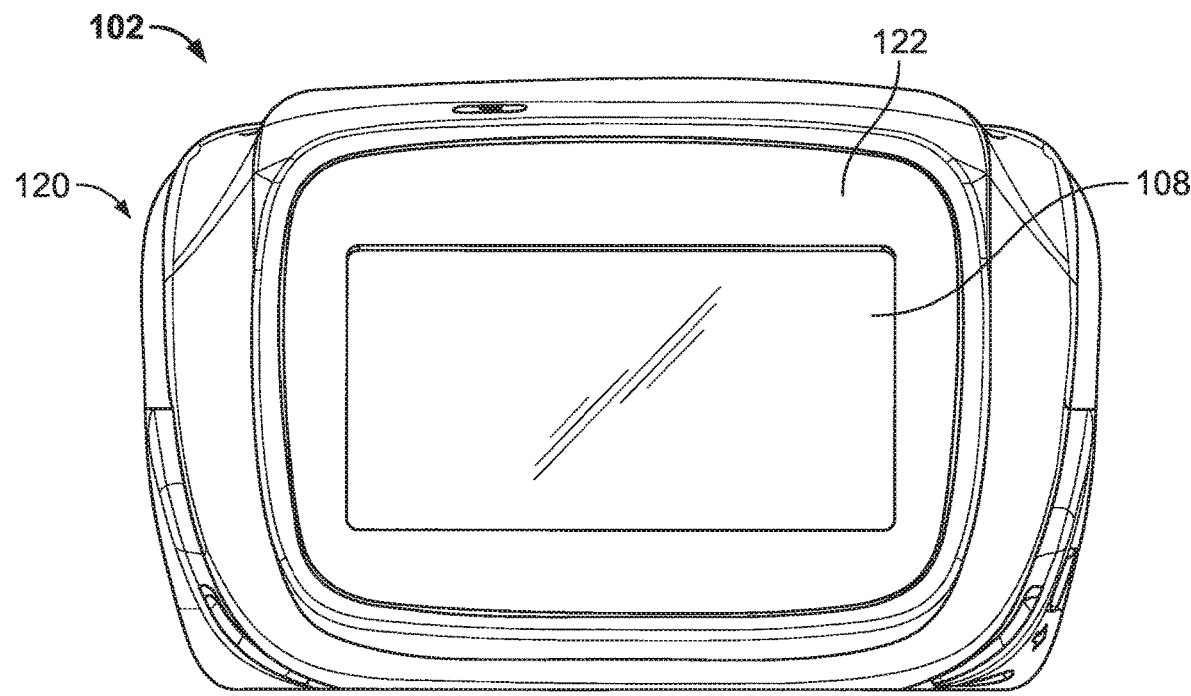
FIG. 4 is a view of the example imaging device from the perspective of a clinician during the eye examination.
Figure 5:
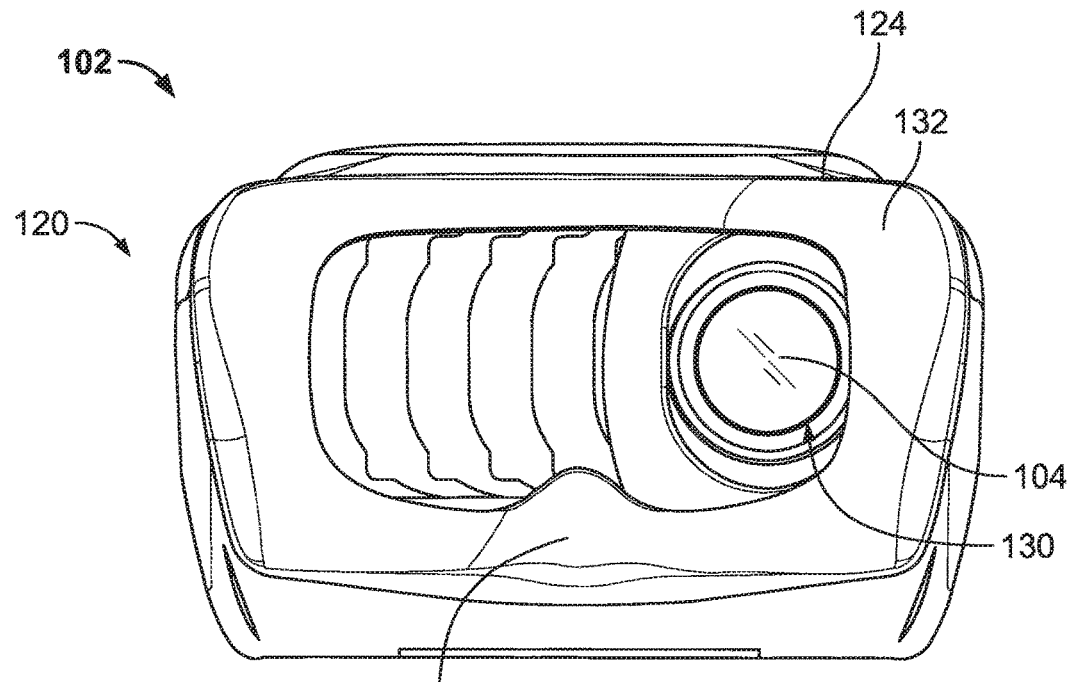
FIG. 5 is a view of the example imaging device from the perspective of a patient during the eye examination.

FIGS. 2 and 3 are isometric views of the imaging device 102. FIGS. 4 and 5 are clinician perspective and patient perspective views, respectively, of the imaging device 102. The imaging device 102 includes a housing 120 having a first end 122 and an opposite second end 124. During use, the first end 122 of the housing 120 can be held by the clinician C or patient P, while the second end 124 of the housing 120 faces one or both eyes of the patient P.

The housing 120 is sized to be hand held. The camera 104, computing device 1800, fundus imaging system 200, and anterior imaging system 300 are located inside the housing 120.

FIG. 4 is a view of the imaging device 102 from the perspective of the clinician C during an eye examination. As shown in FIGS. 2 and 4, the display 108 is supported by the first end 122 of the housing 120. The display 108 displays both images of the eye and controls for capturing those images. In some examples, the display 108 is a liquid crystal display (LCD) and active matrix organic light emitting diode (AMOLED) display. The display 108 can be touch sensitive. For example, the display 108 can be a touchscreen that displays controls for controlling the operation of the imaging device 102 to capture images of the eyes of the patient P by the camera 104. The housing 120 may also support one or more user input buttons near display 108. In some examples, the display 108 can be used to initiate the image capture sequence.

FIG. 5 is a view of the imaging device 102 from the perspective of the patient P during an eye examination. As shown in FIGS. 3 and 5, the second end 124 of the housing 120 has a surface 132 configured to engage the patient P's face. In some examples, the surface 132 is a face cap that at least partially defines a cavity 130. The surface 132 can be positioned against the patient P's face to surround both eyes of the patient P. The camera 104 is positioned inside the cavity 130 at the second end 124 of the housing 120. The face of the patient P can be placed next to the cavity 130 for imaging one or two eyes at a time. In some examples, the camera 104 is configured to move in at least three directions within the imaging device 102 to accomplish imaging both eyes of the patient P when the housing 120 is positioned against the patient P's face.

In some examples, the housing 120 supports positional guides for the patient P, such as a groove 134 where the nose of the patient P is inserted during use or an optional adjustable chin rest. The positional guides can help to align the eye or eyes of the patient P with the cavity 130. Once the patient's P eyes are aligned, the imaging device 102 can initiate image capturing by either the fundus imaging system 200 or the anterior imaging system 300.

Figure 6:
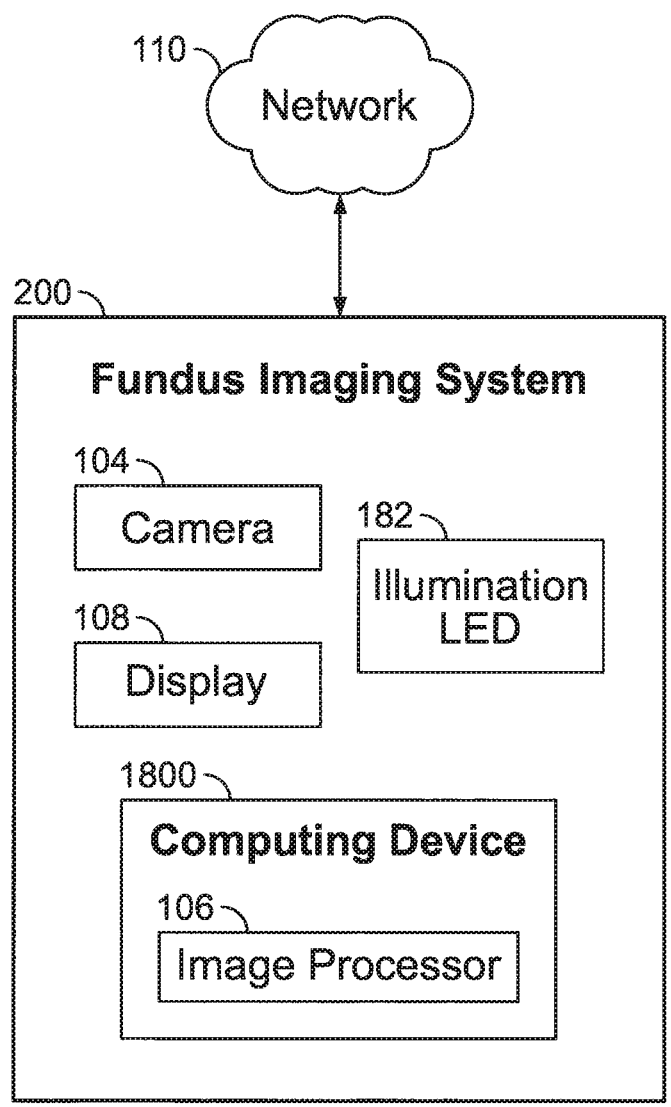
FIG. 6 is a schematic block diagram of an example fundus imaging system.

FIG. 6 is a schematic block diagram of the fundus imaging system 200. The fundus imaging system 200 is similar to the system described in U.S. patent application Ser. No. 16/229,939 filed on even date herewith and/or U.S. patent application Ser. No. 15/054,558 filed on Feb. 26, 2016, the entireties of which are hereby incorporated by reference.

The fundus imaging system 200 functions to create a set of digital images of the fundus of the one or two eyes of the patient P. As used herein, "fundus" refers to the eye fundus and includes the retina, optic nerve, macula, vitreous, choroid and posterior pole. The fundus imaging system 200 can assist the clinician C in screening for, monitoring, or diagnosing various eye diseases, such as hypertension, diabetic retinopathy, glaucoma, and papilledema.

As shown in FIG. 6, the fundus imaging system 200 includes the camera 104 in communication with the image processor 106. The camera 104 is a digital camera including a lens, an aperture, and a sensor array. The lens of the camera 104 can be a variable focus lens, such as a lens moved by a step motor, or a fluid lens, also known as a liquid lens in the art. The camera 104 is configured to record images of one eye at a time. In other examples, the camera 104 is configured to record an image of both eyes substantially simultaneously. In such examples, the fundus imaging system 200 can include two separate cameras, one for each eye.

The example fundus imaging system 200 also includes an illumination light-emitting diode (LED) 182. The illumination LED 182 is connected to the computing device 1800 such that the image processor 106 can coordinate the illumination LED 182 with the adjustment of the variable focus lens and image capture of the camera 104.

The image processor 106 is operatively coupled to the camera 104 and configured to communicate with the network 110 and display 108. The image processor 106 controls the operation of the camera 104. Components of an example computing device 1800, including the image processor 106, are shown in more detail in FIG. 17, which is described further below.

The display 108 is in communication with the image processor 106. In the example imaging device 102 shown in FIGS. 2-5, the display 108 is mounted to the housing 120. In other examples, the display 108 is connected to the image processor 106 by the network 110 and is part of a mobile device such as a smart phone, tablet computer, and the like, or is an external monitor separate from the imaging device 102. The display 108 functions to reproduce images produced by the fundus imaging system 200 in a size and format readable by the clinician C.

The example fundus imaging system 200 is connected to the network 110. The network 110 may include any type of wireless or communication network known in the art. For example, wireless connections can include cellular network connections, Bluetooth, Wi-Fi, radio-frequency identification (RFID), or ZigBee. Other configurations are possible.

Figure 7:
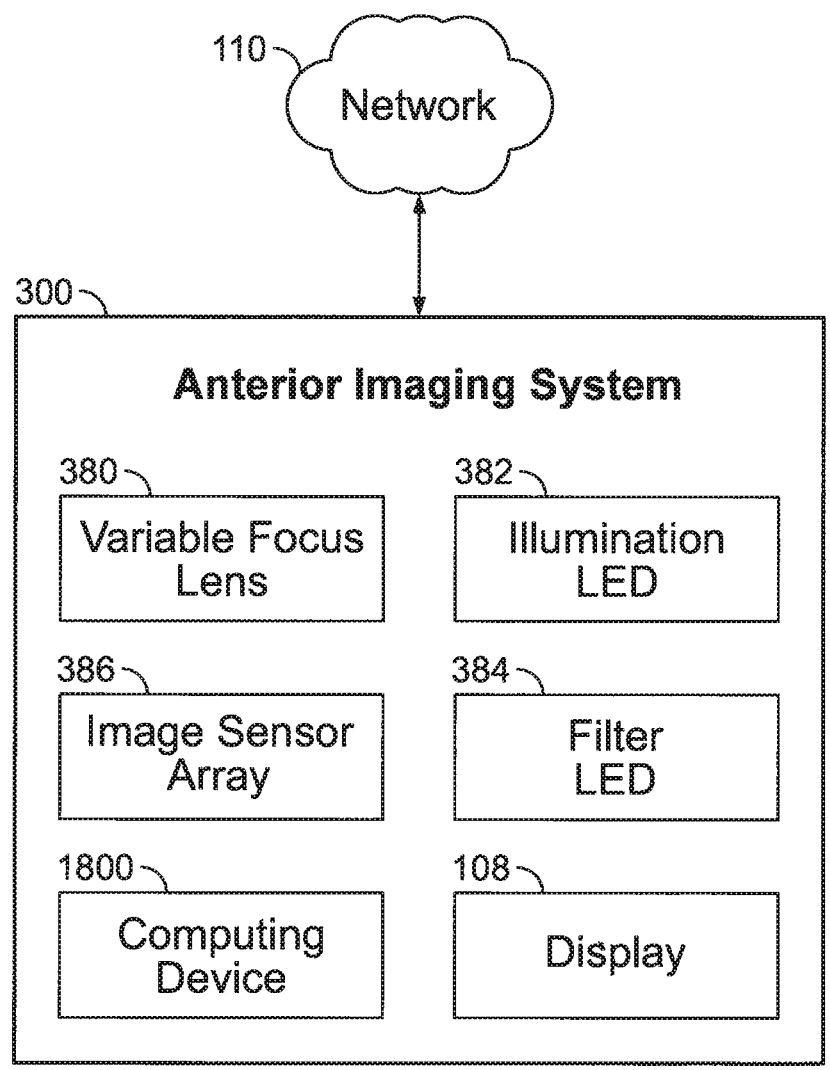
FIG. 7 is a schematic block diagram of an example anterior imaging system.

FIG. 7 is a schematic block diagram of an example anterior imaging system 300. The anterior imaging system 300 shares some of the components used in the fundus imaging system 200 described above such as the display 108, network 110, and computing device 1800. In addition, the anterior imaging system 300 further includes a variable focus lens 380, one or more illumination LEDs 382, one or more filter LEDs 384, and an image sensor array 386, each connected with at least the computing device 1800.

In some examples, the variable focus lens 380 and the image sensor array 386 are part of the camera 104, describe above with respect to the fundus imaging system 200. As described above, the camera 104 is configured to record images of one eye at a time. In other examples, the camera 104 is configured to record an image of both eyes substantially simultaneously. In such examples, the anterior imaging system 300 can include two separate cameras, one for each eye.

In some examples, the variable focus lens 380 is a liquid lens. A liquid lens is an optical lens whose focal length can be controlled by the application of an external force, such as a voltage. In another example, the variable focus lens 380 is one or more movable lenses that are controlled by a stepping motor, a voice coil, an ultrasonic motor, or a piezoelectric actuator.

The image sensor array 386 receives and processes light reflected by the patient's eye. The image sensor array 386 can be a complementary metal-oxide semiconductor (CMOS) sensor array, also known as an active pixel sensor (APS), or a charge coupled device (CCD) sensor. The image sensor array 386 has a plurality of rows and columns of pixels. The image sensor array 386 includes photodiodes each having a light-receiving surface and a substantially uniform length and width. During exposure, the photodiodes convert incident light to a charge. The image sensor array 386 can operate as a global reset such that substantially all of the photodiodes are exposed simultaneously and for substantially identical lengths of time.

The one or more illumination LEDs 382 can be single color or multi-color. For example, the illumination LEDs 382 can be three-channel RGB LEDs, where each die is capable of independent and tandem operation. Optionally, the illumination LEDs 382 can have one or more visible light LEDs and near-infrared LEDs. The optional near-infrared LEDs can provide a preview mode where the clinician C can determine or estimate the patient's P eye focus without illuminating visible light that could cause the pupil to contract or irritate the patient P. For example, in one embodiment, each illumination LED 382 is a single LED or multiple LEDs that provide different colors and/or wavelengths of light needed to illuminate the eye for imaging.

The one or more illumination LEDs 382 are in electrical communication with the computing device 1800. The computing device 1800, and more specifically the image processor 106, is configured to coordinate the illumination of the one or more illumination LEDs 382 with adjustments of the variable focus lens 380 to capture an image of the anterior of the eye. The can include images of the cornea, iris, lens, pupil, eyelids, etc. Various exemplary arrangements of the illumination LEDs 382 will be described with reference to FIGS. 8-15.

The filter LED 384 is in communication with the computing device 1800 and produces a colored light configured to activate a dye. For example, the dye can be applied to the cornea of the patient P's eye, and the light emitted from the filter LED 384 can activate the dye to detect damage to the cornea of the patient P's eye. In some examples, the dye is a fluorescein dye that is applied to the cornea of the patient P's eye using a dropper or a piece of blotting paper. Blinking by the patient P can spread the dye and coat the tear film covering the surface of the cornea. In some examples, the filter LED 384 is a blue LED light that is configured to make any damaged areas on the cornea stained by the dye appear green under the blue light.

FIGS. 8-15 illustrate various arrangements of the one or more illumination LEDs 382 and filter LEDs 384 that can be used for the anterior imaging system 300. As shown, the anterior imaging system 300 includes an optical lens barrel 310 that is configured to move along multiple axes for taking images of the patient P's eyes during an examination conducted by the clinician C. The variable focus lens 380 is located at one end of the optical lens barrel 310, and the image sensor array 386 can be located inside or at an opposite end of the optical lens barrel 310. Alternatively, the image sensor array 386 can be located inside an electrical housing 312.

In FIGS. 8-15, the one or more illumination LEDs 382 are positioned on optical lens barrel 310 in various arrangements around the periphery of the variable focus lens 380. Each arrangement of illumination LEDs 382 is configured to illuminate the cavity 130 at the second end 124 of the housing 120 (see FIGS. 3 and 5) during image capture by the anterior imaging system 300 because the light emitted from the illumination LED 182 of the fundus imaging system 200 is not sufficiently powerful for taking an exterior image of the patient P's eye.

Figure 8:
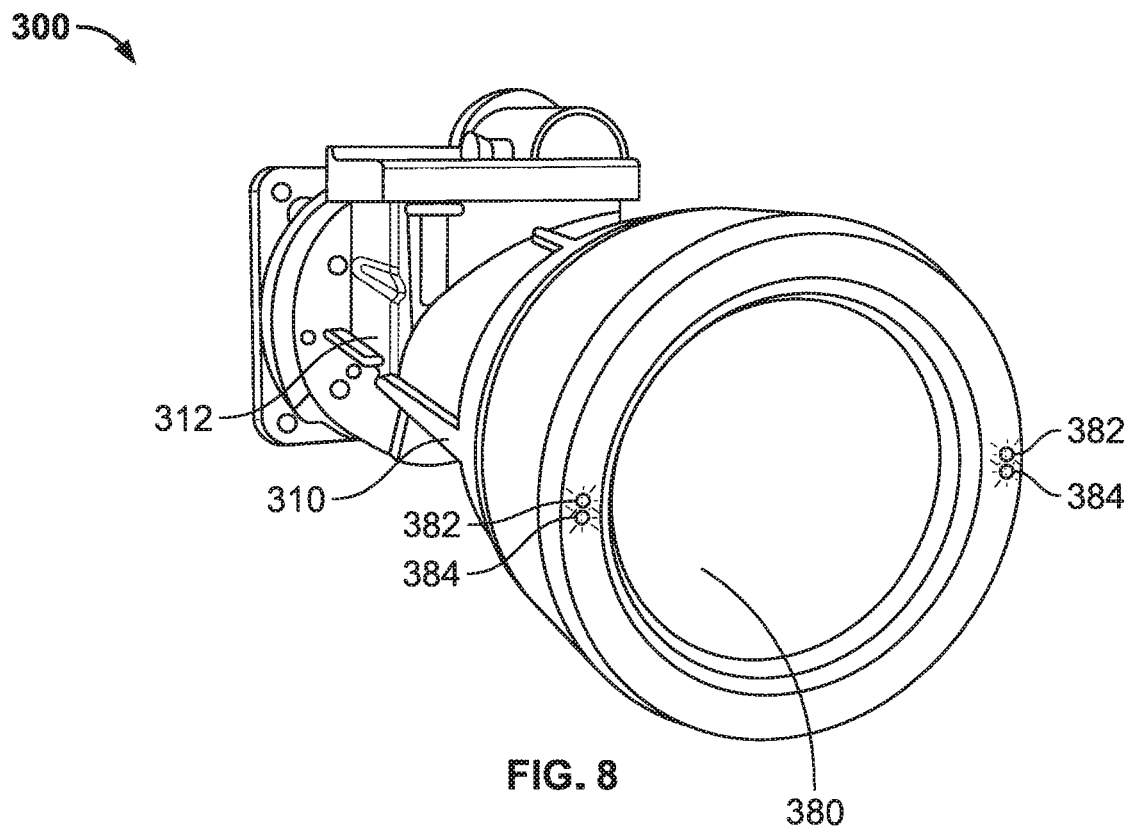
FIG. 8 is an isometric view of an example illumination lighting arrangement for the anterior imaging system.

FIG. 8 is an isometric view of an example illumination lighting arrangement for the anterior imaging system 300. As shown in FIG. 8, the optical lens barrel 310 includes illumination LEDs 382 positioned on opposite sides of the variable focus lens 380. Additionally, the optical lens barrel 310 further includes filter LEDs 384 positioned on opposite sides of the variable focus lens 380. Each filter LED 384 can be positioned next to an illumination LED 382 on the periphery of the optical lens barrel 310 surrounding the variable focus lens 380. In examples where the variable focus lens 380 resembles a clock face having a 12-hour cycle, a first set of illumination LED 382 and filter LED 384 is positioned at the 3 o'clock position, and a second set of illumination LED 382 and filter LED 384 is positioned at the 9 o'clock position.

Figure 9:
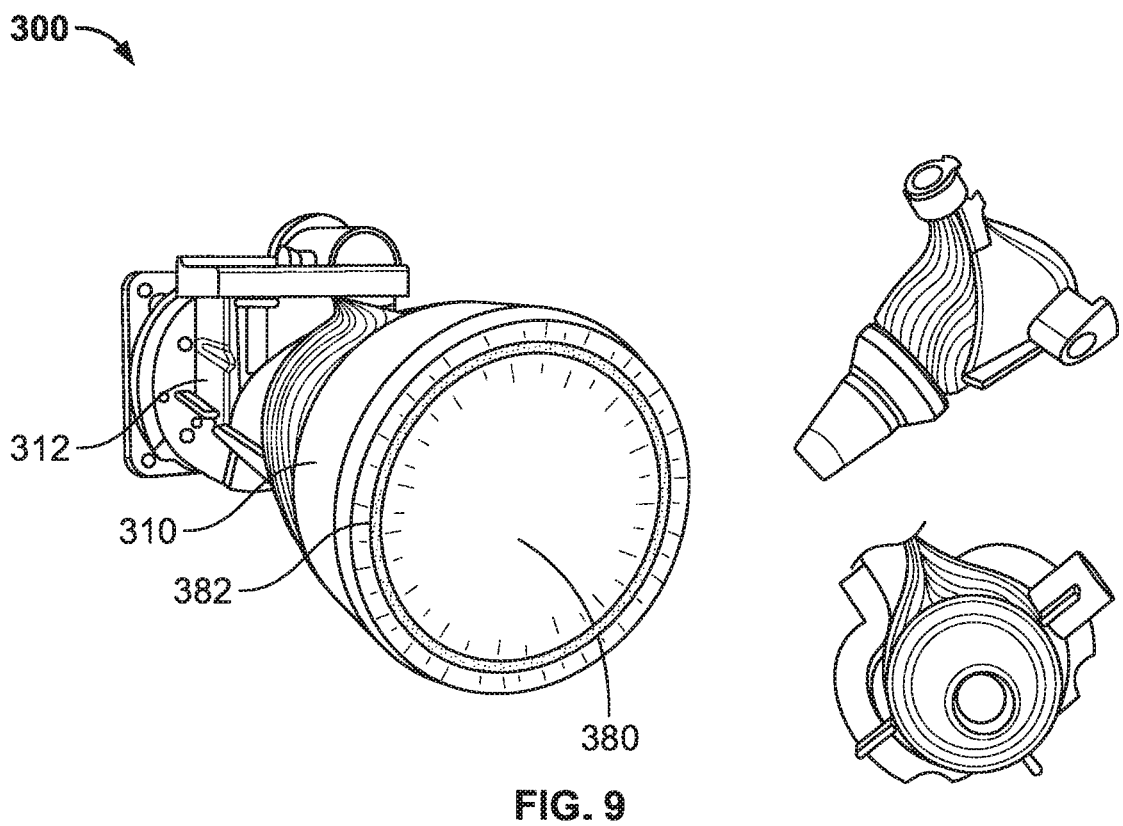
FIG. 9 is an isometric view of another example illumination lighting arrangement for the anterior imaging system.

FIG. 9 is an isometric view of another example illumination lighting arrangement for the anterior imaging system 300. As shown in FIG. 9, the optical lens barrel 310 includes a single illumination LED 382 having a shape that surrounds the periphery of the variable focus lens 380. For example, the illumination LED 382 can have an ellipse shape including circular, oval, coil, ring, and the like shapes that surround the periphery of the variable focus lens 380.

Figure 10:
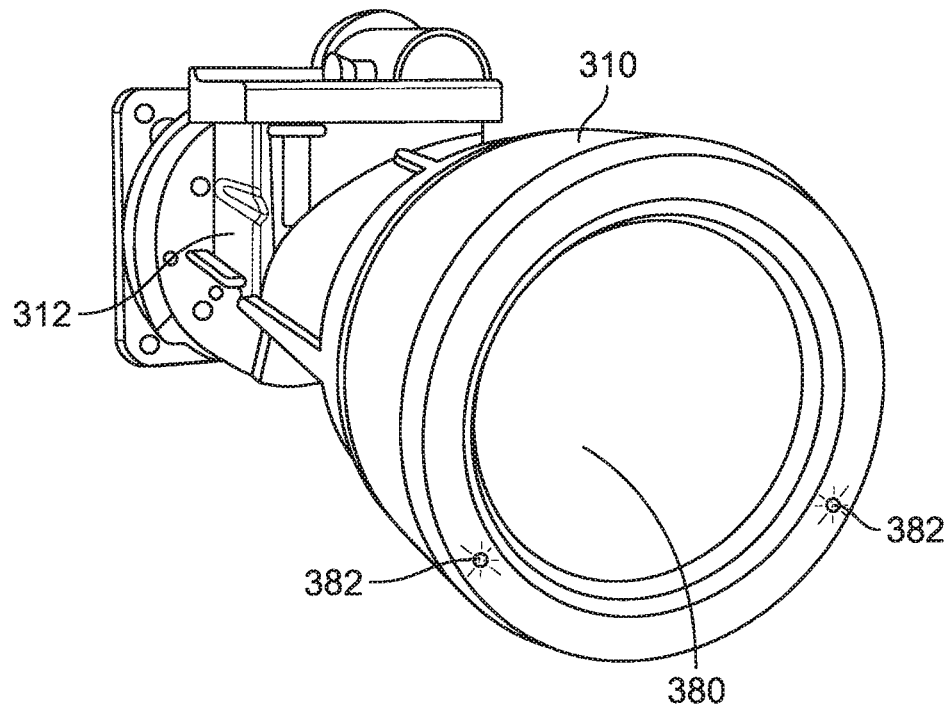
FIG. 10 is an isometric view of another example illumination lighting arrangement for the anterior imaging system.

FIG. 10 is an isometric view of another example illumination lighting arrangement for the anterior imaging system 300. As shown in FIG. 10, the optical lens barrel 310 includes illumination LEDs 382 positioned around the periphery of the variable focus lens 380. For example, a first illumination LED 382 is positioned at the 4 o'clock position and a second illumination LED 382 is positioned at the 8 o'clock position.

In alternative examples, the illumination LEDs 382 are included inside the electrical housing 312, and the light emitted from the illumination LEDs 382 can be piped through the optical lens barrel 310 using fiber optics. For example, in one embodiment, the LEDs can be positioned on an internal component of the imaging device 102, such as a circuit board positioned within the housing 120 of the imaging device 102. Light from the LEDs can be piped from within the imaging device 102 to the periphery of the variable focus lens 380 using fiber optic cables or the like. Accordingly, the light from the illumination LEDs 382 can exit from a front edge of the optical lens barrel 310 using fiber optics.

Figure 11:
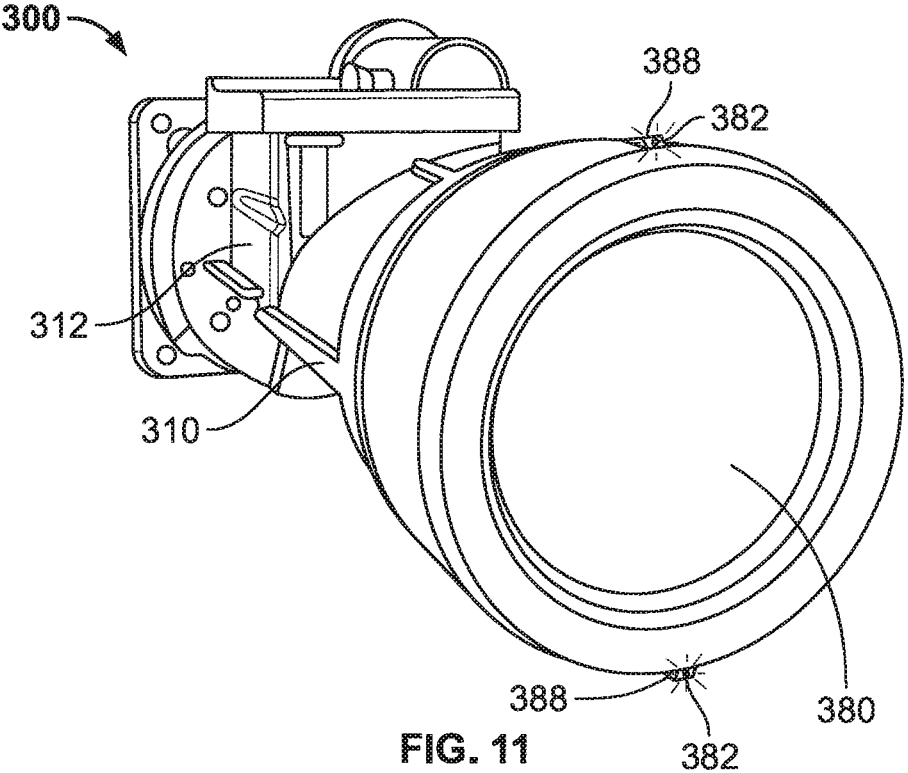
FIG. 11 is an isometric view of another example illumination lighting arrangement for the anterior imaging system.

FIG. 11 is an isometric view of another example illumination lighting arrangement for the anterior imaging system 300. As shown in FIG. 11, the optical lens barrel 310 includes illumination LEDs 382 positioned on angled surfaces 388. Each angled surface 388 extends from the periphery of the optical lens barrel 310 in a radial direction. The angled surfaces 388 and illumination LEDs 382 are configured to face an exterior of the cavity 130 of the imaging device 102 and toward the face of the patient P when the imaging device 102 is positioned against the patient P's face. In the example arrangement of FIG. 11, a first illumination LED 382 is positioned at the 12 o'clock position on the optical lens barrel 310, and a second illumination LED 382 is positioned at the 6 o'clock position on the optical lens barrel 310.

Figure 12:
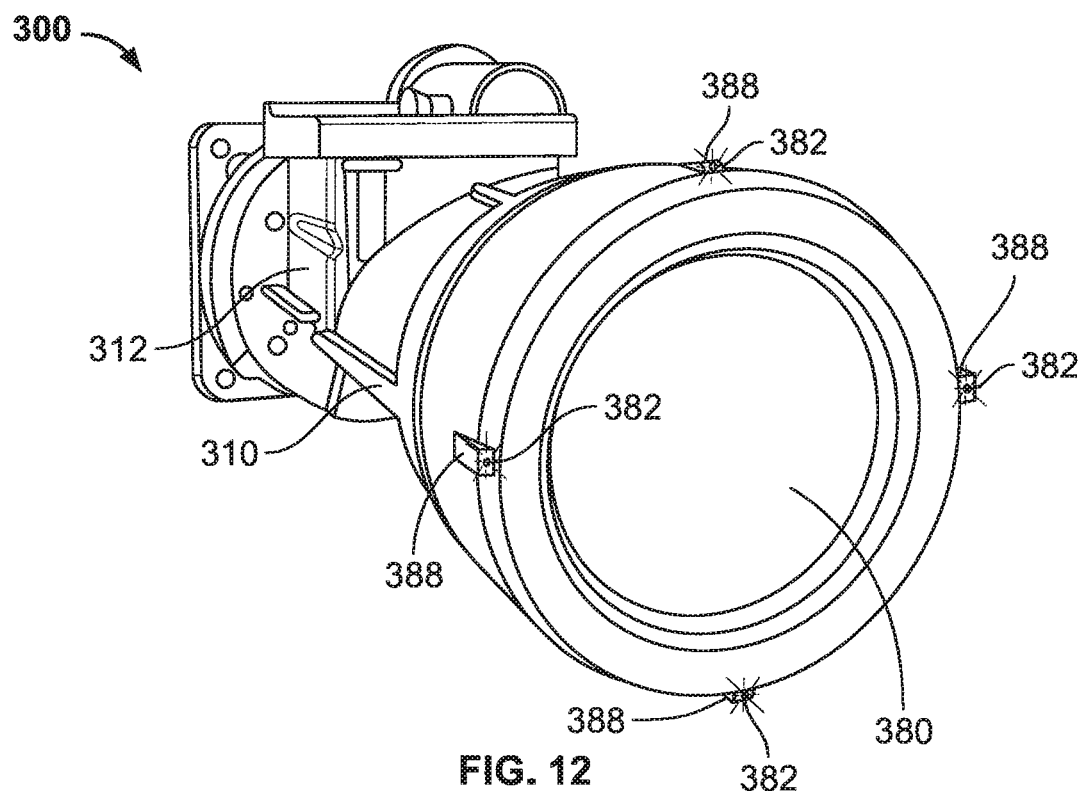
FIG. 12 is an isometric view of another example illumination lighting arrangement for the anterior imaging system.

FIG. 12 is an isometric view of another example illumination lighting arrangement for the anterior imaging system 300. As shown in FIG. 12, the optical lens barrel 310 includes illumination LEDs 382 positioned on angled surfaces 388 around the periphery of the optical lens barrel 310. Each angled surface 388 extends from the periphery of the optical lens barrel 310 in a radial direction and faces an exterior of the cavity 130. In the example of FIG. 12, a first illumination LED 382 is positioned at the 12 o'clock position, a second illumination LED 382 is positioned at the 3 o'clock position, a third illumination LED 382 is positioned at the 6 o'clock position, and a fourth illumination LED 382 is positioned at the 9 o'clock position.

Figure 13:
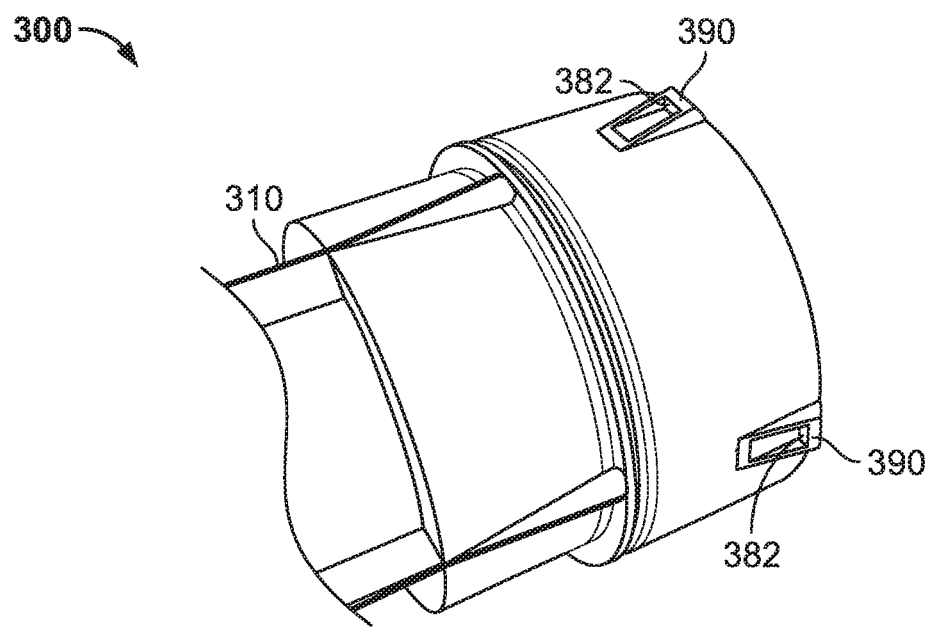
FIG. 13 is an isometric view of another example illumination lighting arrangement for the anterior imaging system.

FIG. 13 is an isometric view of another example illumination lighting arrangement for the anterior imaging system 300. As shown in FIG. 13, the optical lens barrel 310 includes illumination LEDs 382 positioned on angled surfaces 390. Each angled surface 390 extends from the periphery of the optical lens barrel 310 in a radial direction. The angled surfaces 390 and illumination LEDs 382 are configured to face an interior of the cavity 130 and away from the face of the patient P when the imaging device 102 is positioned against the patient P's face. In accordance with the example arrangement of FIG. 13, a first illumination LED 382 can be positioned at the 12 o'clock position, a second illumination LED 382 can be positioned at the 3 o'clock position, a third illumination LED 382 can be positioned at the 6 o'clock position, and a fourth illumination LED 382 can be positioned at the 9 o'clock position.

Figure 14:
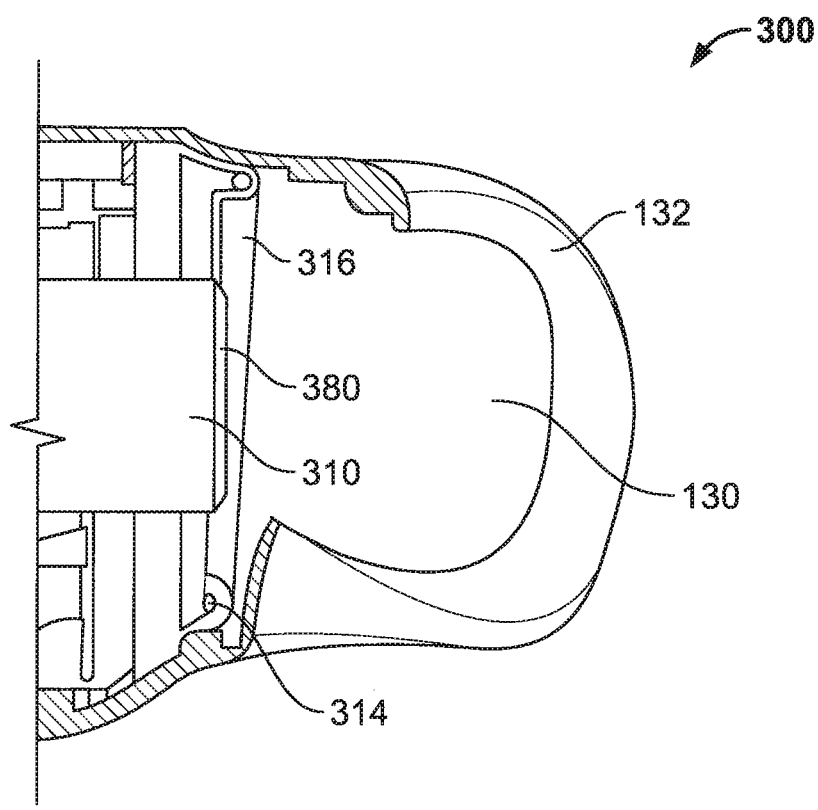
FIG. 14 is a cross-sectional view of another example illumination lighting arrangement for the anterior imaging system.

FIG. 14 is a cross-sectional view of another example illumination lighting arrangement for the anterior imaging system 300. As shown in FIG. 14, the optical lens barrel 310 includes a light pipe 314 generated by one or more illumination LEDs. The light pipe 314 is directed by a light shield 316 around the periphery of the optical lens barrel 310. The light pipe 314 and light shield 316 are configured to indirectly light the cavity 130.

Figure 15:
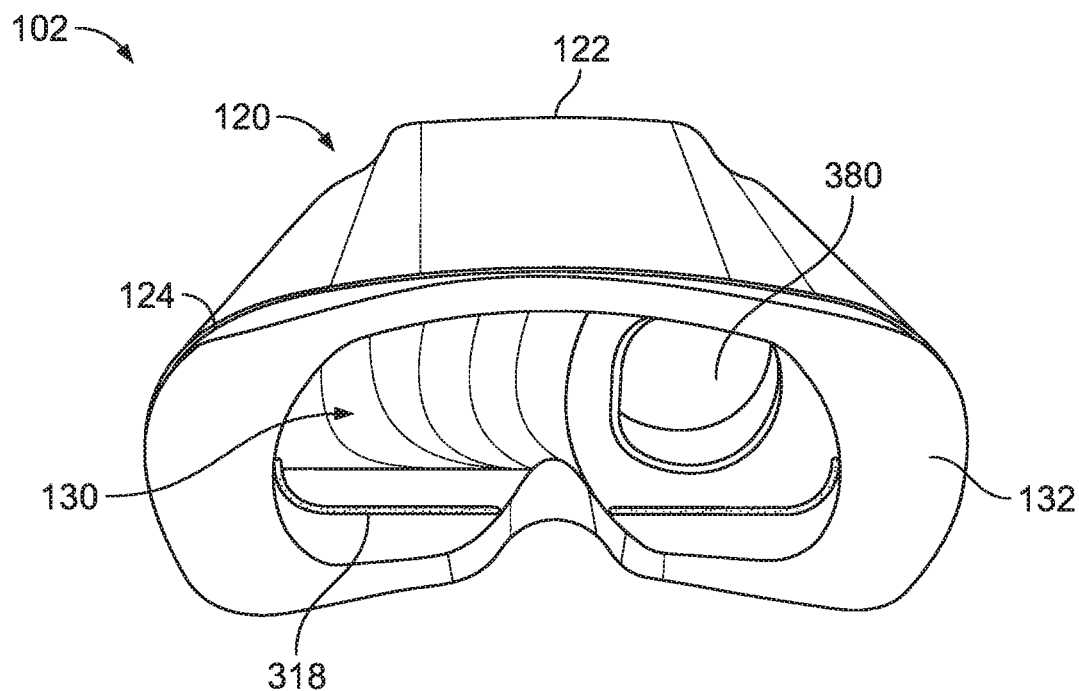
FIG. 15 is an isometric view of another example illumination lighting arrangement for the anterior imaging system.

FIG. 15 is an isometric view of another example illumination lighting arrangement for the anterior imaging system 300. As shown in FIG. 15, an illumination ring 318 is directed around the periphery of the cavity 130 of the imaging device 102. The illumination ring 318 is generated by one or more illumination LEDs and is configured to directly light the cavity 130.

Figure 16:
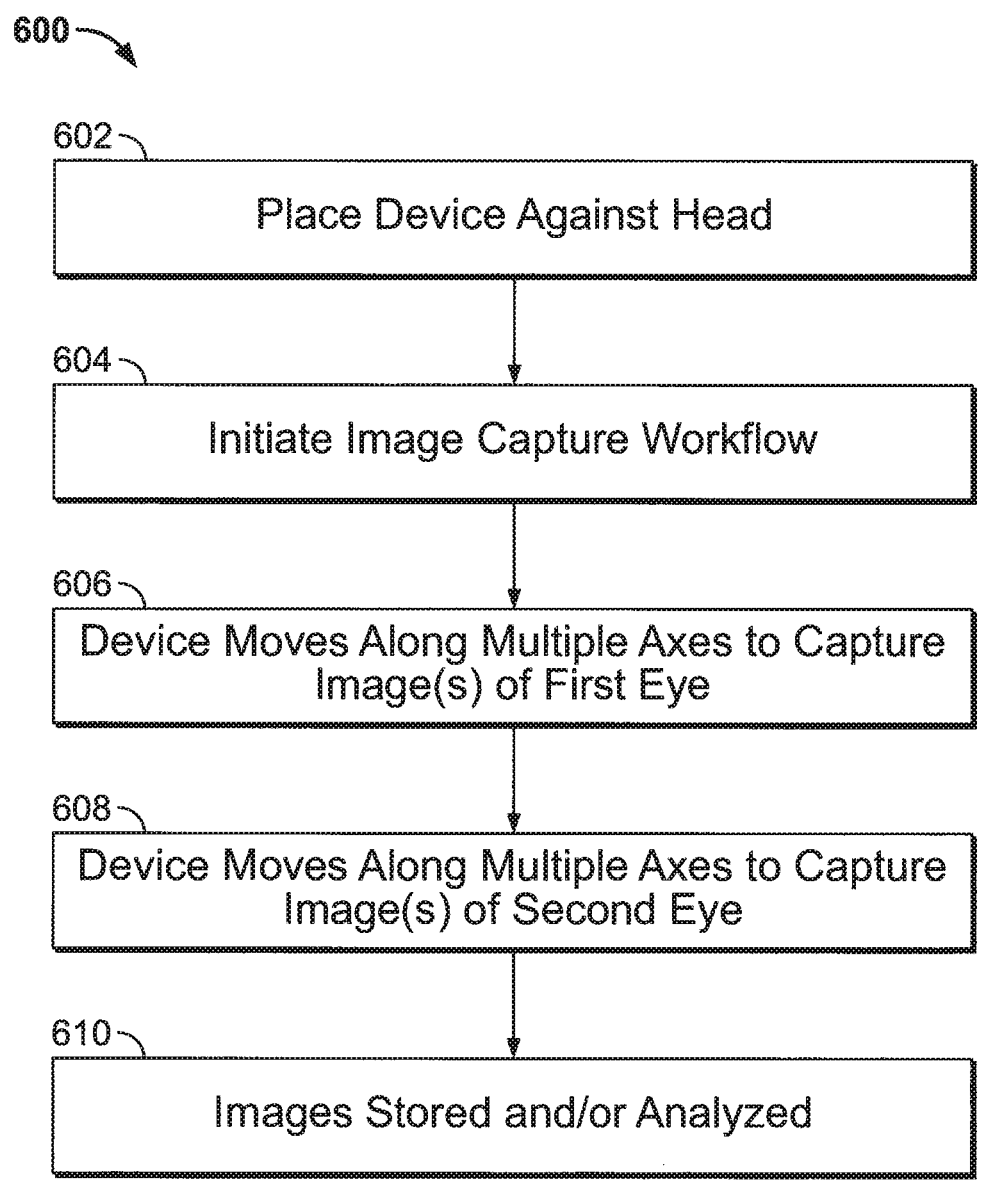
FIG. 16 illustrates an example method of using the anterior imaging system.

FIG. 16 illustrates an example method 600 of using the anterior imaging system 300 for capturing eye images. As shown in FIG. 16, the method 600 includes operation 602 where the imaging device 102 is placed against the face and over the eyes of the patient P by the clinician C (or the patient P can place the imaging device 102 him/herself).

Next, at operation 604, the capture of the images is initiated. One example of a similar workflow is provide in U.S. patent application Ser. No. 15/054,558 filed on Feb. 26, 2016, which is directed to retinal image capturing. In one example, the clinician C uses the display 108 to initiate the workflow for image capture. Alternatively, the workflow can be automatically initiated when the imaging device 102 is placed against the patient P's face.

Next, at operation 606, the optical lens barrel 310 is moved along one or more axes (e.g., X, Y, and Z axes) to position the optical lens barrel 310 inside the cavity 130 to capture one or more images of a first eye. In one example, the imaging device 102 is programmed to automatically move the optical lens barrel 310 along the axes. In another example, the imaging device 102 is programmed to allow the clinician C to manually move the optical lens barrel 310 along the axes (e.g., using controls shown in the display 108).

At operation 606, an image of the cornea of the first eye is captured using the anterior imaging system 300. Operation 606 may include coordinating the illumination of the one or more illumination LEDs 382 with adjustments of the variable focus lens 380 to capture an image of the cornea. As described above, in some examples, the one or more illumination LEDs 382 are positioned on the optical lens barrel 310 in various arrangements around the periphery of the variable focus lens 380. In addition to capturing an image of the cornea of the first eye, operation 606 may include capturing an image of the fundus of the first eye using the fundus imaging system 200. The fundus image may be captured before or after capturing the cornea image.

Once the image(s) of the first eye are complete, control is passed to operation 608, and the optical lens barrel 310 is moved along the x-axis within the cavity 130 of the imaging device 102 to be in position to capture images of a second eye. The optical lens barrel 310 is thereupon moved along the one or more axes (e.g., X, Y, and Z axes) to capture image(s) of the second eye. Again, this movement can be automatic or manual.

At operation 608, an image of the cornea of the second eye is captured using the anterior imaging system 300. Operation 608 may include coordinating the illumination of the one or more illumination LEDs 382 with adjustments of the variable focus lens 380 to capture the image of the cornea. In addition to capturing an image of the cornea of the second eye, operation 608 may further include capturing an image of the fundus of the second eye using the fundus imaging system 200. The fundus image may be captured before or after the cornea image.

Next, at operation 610, the images captured by the imaging device 102 are stored in an internal memory of the imaging device 102. In some examples, at operation 610, the images are analyzed by the clinician C or by another medical professional using the display 108 of the imaging device 102. In some examples, the images are transferred to another device using the network 110 for further analysis by the clinician C or by another medical professional.

Figure 17:
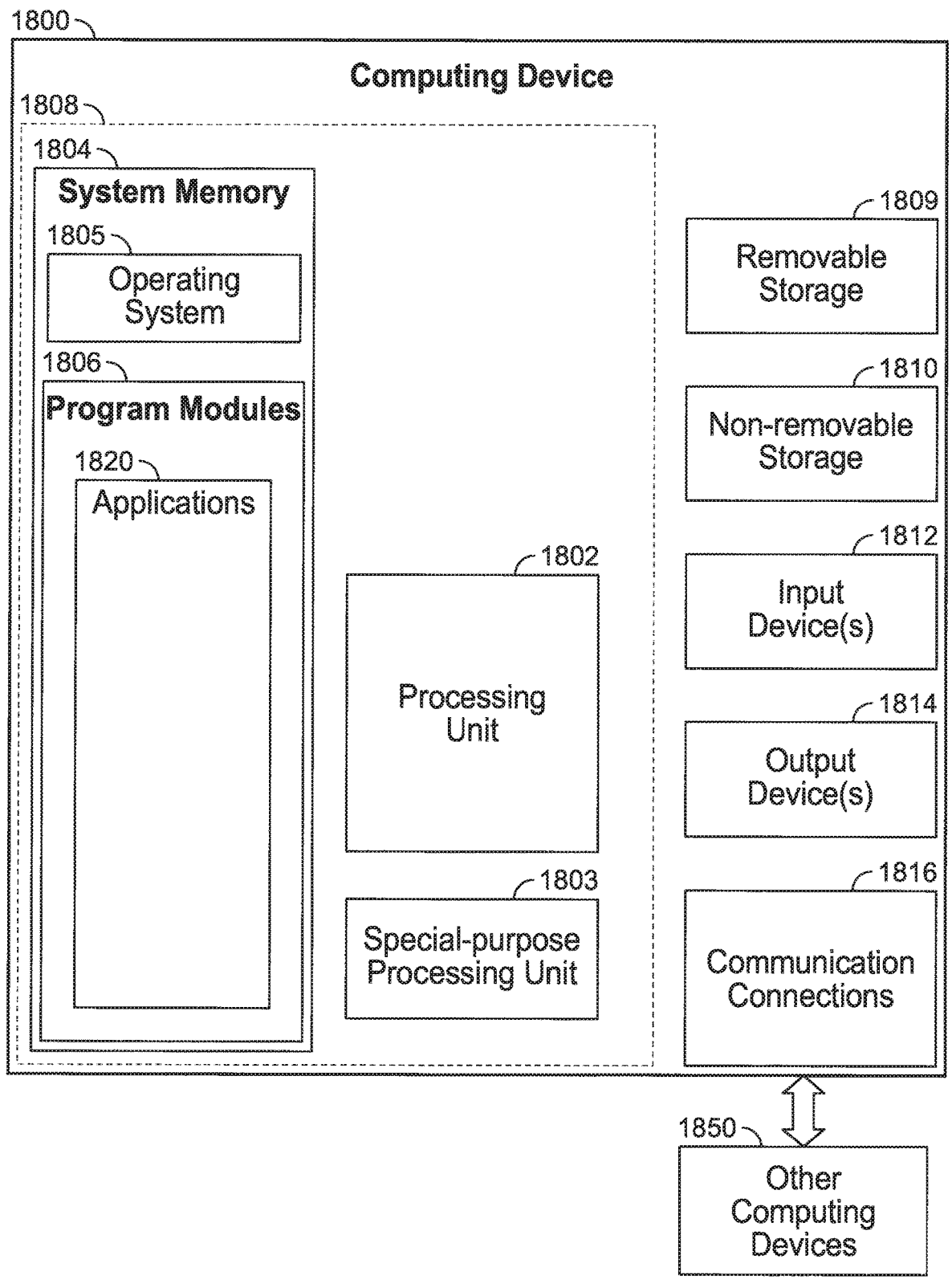
FIG. 17 is a schematic block diagram of a computing device.

FIG. 17 is a block diagram illustrating physical components (i.e., hardware) of a computing device 1800 with which embodiments of the disclosure may be practiced. The computing device components described below may be suitable to act as the computing devices described above, such as the computing devices of the imaging device 102 of FIG. 1, the fundus imaging system 200 of FIG. 6, and the anterior imaging system 300 of FIG. 7.

In a basic configuration, the computing device 1800 may include at least one processing unit 1802 and a system memory 1804. Depending on the configuration and type of computing device, the system memory 1804 may comprise, but is not limited to, volatile storage (e.g., random access memory), non-volatile storage (e.g., read-only memory), flash memory, or any combination of such memories. The system memory 1804 may include an operating system 1805 and one or more program modules 1806 suitable for running software applications 1820. The operating system 1805, for example, may be suitable for controlling the operation of the computing device 1800. Furthermore, embodiments of the disclosure may be practiced in conjunction with a graphics library, other operating systems, or any other application program and is not limited to any particular application or system. This basic configuration is illustrated in FIG. 17 by those components within a dashed line 1808. The computing device 1800 may have additional features or functionality. For example, the computing device 1800 may also include additional data storage devices (removable and/or non-removable) such as, for example, magnetic disks, optical disks, or tape. Such additional storage is illustrated by a removable storage device 1809 and a non-removable storage device 1810.

As stated above, a number of program modules and data files may be stored in the system memory 1804. While executing on the at least one processing unit 1802, the program modules 1806 may perform processes including, but not limited to, generate list of devices, broadcast user-friendly name, broadcast transmitter power, determine proximity of wireless computing device, connect with wireless computing device, transfer vital sign data to a patient's EMR, sort list of wireless computing devices within range, and other processes described with reference to the figures as described herein. Other program modules that may be used in accordance with embodiments of the present disclosure, and in particular to generate screen content, may include electronic mail and contacts applications, word processing applications, spreadsheet applications, database applications, slide presentation applications, drawing or computer-aided application programs, and the like.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. For example, embodiments of the disclosure may be practiced via a system-on-a-chip (SOC) where each or many of the components illustrated in FIG. 17 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, may be operated via application-specific logic integrated with other components of the computing device 1800 on the single integrated circuit (chip). Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

The computing device 1800 may also have one or more input device(s) 1812, such as a keyboard, a mouse, a pen, a sound or voice input device, a touch or swipe input device, etc. The output device(s) 1814 such as a display, speakers, a printer, etc. may also be included. The aforementioned devices are examples and others may be used. The computing device 1800 may include one or more communication connections 1816 allowing communications with other computing devices. Examples of suitable communication connections 1816 include, but are not limited to, RF transmitter, receiver, and/or transceiver circuitry; universal serial bus (USB), parallel, and/or serial ports.

The term computer readable media as used herein may include non-transitory computer storage media. Computer storage media may include volatile and nonvolatile, removable and non-removable media implemented in any method or technology for storage of information, such as computer readable instructions, data structures, or program modules. The system memory 1804, the removable storage device 1809, and the non-removable storage device 1810 are all computer storage media examples (i.e., memory storage.) Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 1800. Any such computer storage media may be part of the computing device 1800. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Although the example medical devices described herein are devices used to monitor patients, other types of medical devices can also be used. For example, the different components of the CONNEX™ system, such as the intermediary servers that communication with the monitoring devices, can also require maintenance in the form of firmware and software updates. These intermediary servers can be managed by the systems and methods described herein to update the maintenance requirements of the servers.

Embodiments of the present invention may be utilized in various distributed computing environments where tasks are performed by remote processing devices that are linked through a communications network in a distributed computing environment.

The block diagrams depicted herein are just examples. There may be many variations to these diagrams described therein without departing from the spirit of the disclosure. For instance, components may be added, deleted or modified.

The systems and method described herein result in a significant technical advantage. For example, the computing devices can be programmed to more efficiently capture both fundus and anterior eye images. This allows the computing devices to accomplish an analysis of a greater number of images in a smaller amount of time.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless whether shown and described in combination or separately, the various features (both structural and methodological) are intended to be selectively included or omitted to produce an embodiment with a particular set of features.

Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. An anterior imaging system, comprising:
a housing defining a cavity, the housing having a first end and a second end, the cavity being defined at the second end between a camera and a surface being configured to surround both first and second eyes of a patient, the camera including an optical lens barrel positioned at least partially inside the cavity, and a variable focus lens;
one or more illumination LEDs positioned inside the cavity around the periphery of the optical lens barrel, and being configured to illuminate an anterior portion of one of the patient's first and second eyes within the cavity for imaging the first and second eyes by the camera and the variable focus lens; and
a light pipe generated by the one or more illumination LEDs, the light pipe being directed by a light shield around the periphery of the optical lens barrel and configured to indirectly light the cavity between the camera and the surface that surrounds the first and second eyes of the patient.

2. The anterior imaging system of claim 1, further comprising filter LEDs positioned on the optical lens barrel and at opposite sides of the variable focus lens.

3. The anterior imaging system of claim 1, wherein the camera is configured to capture images of a cornea and a fundus of the eye.

4. An imaging device comprising:
a housing having a surface configured to engage the face of a patient, the housing having a first end and a second end;
a cavity at least partially defined by the housing, the cavity being defined at the second end of the housing where a surface being configured to surround both first and second eyes of the patient is located;
an anterior imaging system having an optical lens barrel positioned at least partially inside the cavity and having a variable focus lens at one end, and an image sensor array at an opposite end;
one or more illumination LEDs positioned inside the cavity around the periphery of the optical lens barrel and at opposite sides of the variable focus lens, and being configured to illuminate the cavity for imaging the first and second eyes;
a light pipe generated by the one or more illumination LEDs, the light pipe being directed by a light shield around the periphery of the optical lens barrel and configured to indirectly light the cavity between the anterior imaging system and the surface that surrounds the first and second eyes of the patient; and
a processing device and at least one non-transitory computer readable data storage device storing instructions that, when executed by the processing device, cause the imaging device to control the illumination of the one or more illumination LEDs with adjustments of the variable focus lens to capture an image of an anterior portion of the first or second eye.

5. The imaging device of claim 4, further comprising a fundus imaging system, and the instructions further cause the imaging device to capture an image of the fundus.

6. The imaging device of claim 4, wherein the instructions further cause the imaging device to move the optical lens barrel along one or more axes to position the optical lens barrel inside the cavity to capture one or more images of the first eye and the second eye.

7. A method for capturing eye images, the method comprising:
receiving initiation of a workflow to capture one or more eye images;
moving an optical lens barrel along x, y, and z axes to position the optical lens barrel proximate a first eye, the optical lens barrel being positioned at least partially inside a cavity covering both the first eye and a second eye of a patient, the cavity being positioned at an end of a housing of an anterior imaging system between a camera and a surface being configured to surround the first eye and the second eye of a patient;
controlling illumination of the cavity by one or more illumination LEDs with adjustments of a variable focus lens to capture a cornea image of the first eye, the one or more illumination LEDS positioned inside the cavity and around the variable focus lens;
moving the optical lens barrel inside the cavity along the along x, y, and z axes to position the optical lens barrel proximate the second eye;
coordinating the illumination of the cavity by the one or more illumination LEDs with adjustments of the variable focus lens to capture a cornea image of the second eye; and
storing the one or more images of the first eye and the second eye; and
wherein a light pipe is generated by the one or more illumination LEDs, the light pipe being directed by a light shield around the periphery of the optical lens barrel and configured to indirectly light the cavity between the camera and the surface that surrounds the first eye and the second eye of the patient.

8. The method of claim 7, further comprising capturing fundus images of the first eye or the second eye.

* * * * *